United States Patent [19]

Li

[11] 4,427,419

[45] Jan. 24, 1984

[54] SEMIPERMEABLE MEMBRANES PREPARED FROM POLYMERS CONTAINING PENDENT SULFONE GROUPS

[75] Inventor: George S. Li, Macedonia, Ohio

[73] Assignee: The Standard Oil Company, Cleveland, Ohio

[21] Appl. No.: 357,366

[22] Filed: Mar. 12, 1982

[51] Int. Cl.$^3$ .............................................. B01D 53/22
[52] U.S. Cl. ........................................ 55/16; 55/68; 55/158
[58] Field of Search ........................... 55/16, 68, 158; 210/500.2

[56] References Cited

U.S. PATENT DOCUMENTS

| | | | |
|---|---|---|---|
| 3,259,592 | 7/1966 | Fox et al. | 430/62 X |
| 3,350,844 | 11/1967 | Robb | 55/16 |
| 3,534,528 | 10/1970 | Porter | 55/16 |
| 3,709,774 | 1/1973 | Kimura | 55/16 X |
| 3,735,559 | 5/1973 | Salemme | 55/16 |
| 3,780,496 | 12/1973 | Ward et al. | 55/16 |
| 3,994,860 | 11/1976 | Brousse | 210/500.2 X |
| 4,029,582 | 6/1977 | Ishii et al. | 55/16 X |
| 4,208,508 | 6/1980 | Hashino et al. | 210/500.2 X |
| 4,230,463 | 10/1980 | Henis et al. | 55/16 |
| 4,273,903 | 6/1981 | Rose | 210/500.2 X |
| 4,286,015 | 8/1981 | Yoshida et al. | 210/500.2 X |
| 4,351,860 | 9/1982 | Yoshida et al. | 210/500.2 X |

*Primary Examiner*—Robert H. Spitzer
*Attorney, Agent, or Firm*—D. L. Pawl; Gary R. Plotecher; Larry W. Evans

[57] ABSTRACT

Semipermeable membranes useful for separating gaseous mixtures of carbon dioxide and methane into enriched fractions of each are prepared from at least one polymer containing a preponderance of arylene units, such as polyxylene oxide, the arylene units containing pendent sulfone groups substituted with an aromatic group, such as phenyl.

10 Claims, No Drawings

SEMIPERMEABLE MEMBRANES PREPARED FROM POLYMERS CONTAINING PENDENT SULFONE GROUPS

BACKGROUND OF THE INVENTION

1. Field of the Invention

This invention relates to semipermeable membranes. In one aspect, the invention relates to semipermeable membranes prepared from polymers containing pendent sulfone groups while in another aspect, the invention relates to the use of these membranes to separate various gaseous mixtures, such as carbon dioxide and methane, into enriched fractions of their constituent parts.

2. Description of the Prior Art

The art is replete with teachings describing various semipermeable membranes, their preparation and use. Robb, U.S. Pat. No. 3,350,844, teaches the enrichment of gases by permeation through a thin permeable film or membrane prepared from a polyarylene oxide film. Ward and Salemme, U.S. Pat. No. 3,780,496, teach the use of sulfonated polyxylylene oxide membranes to separate helium, hydrogen and oxygen from gas mixtures.

While the membranes of the above teachings and others all display some level of utility, there exists a continuing search for new membranes and new applications for both new and known membranes. One application where the use of membrane technology may prove beneficial is in the separation of gaseous carbon dioxide-methane mixtures into enriched fractions of their constituent parts. Natural gas is generally found in combination with carbon dioxide. Removal of the carbon dioxide from the natural gas is desirable because it results in both a product (purified natural gas) of greater commercial worth and it provides purified carbon dioxide useful for other applications, such as enhanced oil recovery. Conventional separation processes generally employ cryogenic methods which are relatively energy intensive.

SUMMARY OF THE INVENTION

The subject of this invention is a semipermeable membrane useful for separating a gaseous mixture of carbon dioxide and methane into enriched fractions of each, the membrane formed from at least one polymer containing a preponderance of arylene units of the formula

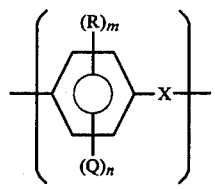

(I)

where
each R is independently $C_1$–$C_8$ aliphatic or a $C_5$–$C_7$ cycloaliphatic hydrocarbon radical, an aryl radical, an aralkyl radical or an alkaryl radical, each radical being free of a tertiary α-carbon atom;
each Q is a radical of the formula

(II)

where R′ is a nonpolymeric aryl radical;
X is a divalent oxygen or sulfur atom or a carbonate group;
m is an integer of 0–2; and
n is 0–1 with the proviso that n is 1 in at least 10 percent of the arylene units of the polymer.

These membranes can be used in other applications, including reverse osmosis processes, and are easily prepared. Moreover, these membranes demonstrate good durability.

DETAILED DESCRIPTION OF THE INVENTION

The membrane of this invention is prepared from at least one polymer containing a preponderance of arylene units of formula I. As here used, the term "preponderance" means that at least 50%, preferably at least 55%, of the units of the polymer are arylene units of formula I. In those polymers where the arylene units comprise less than essentially 100% of the total units of the polymer, the other units can be of essentially any structure that does not prevent the polymer from being fabricated into a membrane useful for separating a gaseous mixture of carbon dioxide and methane to enriched fractions of each. These other units can be incorporated into the polymer to serve simply as a diluent to the arylene units or to impart specific properties to the polymer which will eventually be manifested in the membrane, properties such as tensil strength, hydrophilicity, hydrophobicity, etc. These other units must also be able to polymerize with the arylene units in a manner sufficient to allow formation of polymers of adequate molecular weight, e.g. at least about 20,000 weight average molecular weight. These other units include monomers that polymerize through an ethylenically unsaturated bond, such as ethylene, styrene, etc.; through a hydroxy group, such as diethylene glycol; through an amine group, such as ethylene diamine; and the like. Preferably, polymers here used to form the membranes of this invention contain no significant amount of structural units other than the arylene units of formula I, i.e. polymers consisting essentially of arylene units of formula I.

As noted above, X can be divalent oxygen, —O—, divalent sulfur, —S—, or a carbonate group

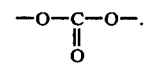

As the term "independently" implies, the definition of X can vary from arylene unit to arylene unit and thus a polymer consisting essentially of arylene units of formula I can contain all three linkages although preferably the X linkage has the same definition throughout the polymer, i.e. all carbonate, all oxygen or all sulfur. Divalent oxygen is the preferred definition of X.

Typical groups represented by R in formula I include methyl, ethyl, propyl, hexyl, cyclohexyl, cyclohexenyl, phenyl, tolyl, xylenyl, phenethyl, and the like. If desired, R can contain inert substituents, i.e. substituents that are nonreactive with the components of the permeant under separation conditions, although preferably R is free of any such substituents. If R is present (m is 1 or 2) then preferably it is dependently a $C_1$-$C_4$ alkyl radical, most preferably a methyl radical. When m is 0, R is not present.

R' in the definition of Q can be any nonpolymeric aryl radical, such as phenyl, tolyl, xylenyl and phenethyl. By "nonpolymeric" is meant that the aryl radical is not part of a polymer chain, i.e. the aryl radical of an arylene unit of another polymer strand of formula I or in other words, the sulfone group,

does not link two independent polymer strands. However the aryl radical here includes multi-ring compounds such as biphenyl, naphthyl, diphenyloxide, etc. Preferred aryl radicals are phenyl, tolyl, xylenyl and phenethyl.

Of the total number of arylene units formula I in any given polymer, at least 10% of those arylene units contain the substituent Q (n is 1). Preferably, at least 20% of the arylene units of the polymer contain Q and most preferably, at least 30%. These percent figures assume a polymer consisting essentially of arylene units of formula I and thus the percent of arylene units containing Q and those polymers containing structural units other than those of formula I should be increased accordingly. For example, if 75% of the structural units of the polymer are formula I, then the minimal number of arylene units containing Q should be at least 30% higher than in a comparable polymer of essentially 100% arylene units.

R' is preferably an aryl radical of the formula

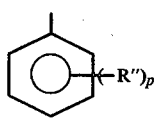

(III)

where
each R" is independently a $C_1$-$C_6$ aliphatic radical, and
is an integer of 0–4.

If p is a positive integer (greater than 0), preferably it is 1 or 2 and if p is a positive integer, then R" is preferably at $C_1$-$C_3$ alkyl radical.

In a preferred embodiment of this invention, the semipermeable membrane is prepared from a polyphenylene ether having a repeating structural unit of formula I where X is divalent oxygen and m and n are 0. The weight average molecular weight of this material is typically at least about 20,000 and preferably at least about 50,000. The maximum weight average molecular weight is limited only by practical considerations, particularly the film-forming ability of the polymer, but typically it does exceed about 1,000,000 weight average molecular weight. These polymers and their preparation are defined at length in Robb, U.S. Pat. No. 3,350,844.

The polyphenylene oxide polymer described in the above paragraph can be readily converted to a polymer having a repeating structural unit of formula I where X is oxygen by contacting the polymer with chlorosulfonic acid as the sulfonating agent. This will sulfonate the benzene nucleus of the arylene unit, the sulfur being present in either a sulfonic acid group, —$SO_3H$, or in a sulfonyl chloride group, —$SO_2Cl$. This procedure is defined in greater detail by Fox et al., U.S. Pat. No. 3,259,592 (except polyxylene oxide is used instead of polyphenylene oxide) and this teaching is here incorporated by reference. The sulfonated polyphenylene oxide is then converted to a polyphenylene oxide containing Q groups by contacting the sulfonated resin with an aromatic compound, such as benzene, toluene, xylene, and/or ethylbenzene. The temperature and pressure at which this second step can be performed can vary widely but is typically conducted at a temperature between about 100° and about 150° C. and preferably between about 110° and about 140° C. The pressure at which this reaction takes place can vary the sub- to superatmospheric pressure. Generally, an amount in excess of stochiometric requirements an aromatic compound is employed to insure complete reaction of all available sulfonic acid and/or sulfonyl chloride groups.

The polymers of this invention can be prepared by other methods such as reacting a polyphenylene oxide polymer containing halogen with a salt of an aromatic sulfonic acid or reacting a polymer containing some anion, such as lithium, with a chlorosulfonyl aromatic. However, the method described in the preceding paragraph is generally preferred due to its relative convenience. The reactions of this preferred method are typically conducted in the presence of a suitable solvent, such as chloroform.

The semipermeable membrane can be manufactured by any conventional method. In one embodiment, the polymer is dissolved in some suitable solvent to form about a 5 to about a 20, preferably a 7 to about a 15, wt % solution. Generally any polar solvent can be employed with chloroform, dimethylformamide, dimethylsulfoxide, dimethylacetamide, acetone and methylethyl ketone being exemplary. The solution is then poured over a clean glass plate and spread eveningly to a uniform thickness with the aid of a doctor's blade. The membranes are then air dried, removed from the glass plate and further dried in air under ambient conditions for suitable period of time, generally in excess of 24 hours. In other embodiments, these membranes can be manufactured by the various laboratory and commercial techniques known in the art. These membranes can also be manufactured in structures other than films, such as hollow fibers.

The membranes of this invention can be cast at any desirable thickness although membranes having a thickness between 25 mils (1 mil equals 25 micrometers) and 1,000 angstroms, preferably between 10 mils and 1,000 angstroms. These membranes demonstrate good permeability, durability, flexibility, strength and corrosion resistance.

The semipermeable membranes of this invention find particular utility for the separation of gaseous carbon dioxide-methane mixtures into their constituent parts, i.e. enriched fractions of carbon dioxide and methane. However, these membranes also have utility for separating other gaseous mixtures, such as those containing oxygen, nitrogen, helium, and the like. These membranes are also useful for separating liquid mixtures, such as ethanol-water, water-aldehyde, salt water, carboxylic acid-water, etc. If used to separate liquid mixtures into their constituent parts, then these membranes are used in the same manner as known membranes for these separations. Furthermore, these membranes can be used in any one of a number of different manners including reverse osmosis and pervaporation, the latter being a combination of permeation and evaporation.

The following examples are illustrative of specific embodiments of this invention and unless indicated to the contrary, all parts and percentages are by weight.

SPECIFIC EMBODIMENTS

Polymer Preparation

The polymers here used to manufacture the membranes are all based upon polyphenylene oxide (weight average molecular weight of about 46,000). A typical preparation of the polymer commenced with contacting polyphenylene oxide dissolved in chloroform with a stochiometric excess of chlorosulfonic acid, also dissolved in chloroform. Chlorosulfonated-polyphenylene oxide precipitated from the chloroform, was recovered and then further reacted at an elevated temperature (typically about 120° C.) with an aromatic compound, such as benzene, toluene, etc. The final dark solution was then cooled, precipitated with methanol, washed with dilute sodium bicarbonate, and dried.

Membrane Preparation

All the membranes here tested were prepared from the arylsulfonated polyphenylene oxide polymers prepared by the above description. The membrane was prepared by mixing a dilute (about 5 to about 20 wt %) solution of polymer in a suitable solvent, typically about 7 wt %, poured over a clean glass plate and spread eveningly to a uniform thickness with the aid of a doctor's blade, air dried, removed from the glass plate, and further dried in air at ambient conditions for at least 24 hours.

Apparatus and Procedure

A modified Gilbert cell was used to test the permeation of the films. The test side was exposed to a carbon dioxide/methane/nitrogen mixture in a mole ratio of 2.99:32:65. The permeant was picked up by a carrier gas, helium, and injected intermittently through a sample valve into a GC column for analysis. The experiments were conducted at 23° C., the partial pressure of the test gas on the feed side was 29.7 psi and the partial pressure of the product gas on the permeant side was about 0 and purged with 29.77 psi helium at a flow rate much in excess of the permeation rate. The area of the test membrane was 7.07 square inches. The film thickness was about 1–2 mils.

The carbon dioxide permeability and carbon dioxide/methane selectivity figures are reported in the following Table. The sulfur content of the modified polymers from which the membrane was formed is given in weight percent and the aryl portion of the sulfone group, i.e. R', is listed separately.

TABLE

SEPARATION CHARACTERISTICS OF SEMIPERMEABLE MEMBRANES PREPARED FROM VARIOUS POLYPHENYLENE OXIDE POLYMERS

| Ex | R' | Sulfur Content (Wt %) | Separation Factor | $CO_2$ Permeation Factor $\frac{CM^3 \cdot CM \cdot 10^{-10}}{CM^2 \cdot CM (Hg) \cdot sec}$ |
|---|---|---|---|---|
| 1 | Tolyl | 7 | 24 | 121 |
| 2 | M—Xylenyl | 2.5 | 22 | 99 |
| 3 | Phenyl | 4.7 | 21 | 135 |
| 4 | Ethylbenzyl | 2.8 | 18 | 100 |
| A* | none | 0 | 18 | 87 |
| B** | none | — | 37 | 27 |

*Membrane prepared from unmodified polyxylene oxide.
**Membrane prepared from sulfonated polyxylene oxide, sulfur content not measured.

The above data clearly demonstrates the general superiority of membranes formed from aryl sulfonated polypropylene oxide polymers. The membrane formed from the toluene sulfonated polypropylene oxide polymer was ⅓ better than the membrane prepared from unmodified polypropylene oxide in both carbon dioxide permeability and selectivity. Membranes formed from these modified polypropylene oxide polymers have also been shown to be essentially impervious to boiling water while membranes formed from sulfonated polypropylene oxide are generally water swellable.

The separation factor was calculated by the following formula $$\frac{CO_2 \text{ Permeation Factor}}{CH_4 \text{ Permeation Factor}}$$

The permeation factor is expressed as the quotient of the product of product gas volume ($CM^3$, STP) times membrane thickness (CM) divided by the product of membrane surface area ($CM^2$) times the pressure differential across the membrane (CM Hg) times the period of separation (sec). The factor $10^{-10}$ is used simply for convenience.

While this invention has been described in considerable detail by the preceding examples, this detail is provided for the purpose of illustration only and is not to be construed as limitations upon the invention as described in the following claims.

What is claimed is:

1. A semipermeable membrane useful for separating a gaseous mixture of $CO_2$ and $CH_4$ into enriched fractions of each, the membrane formed from at least one polymer containing a preponderance of arylene units of the formula

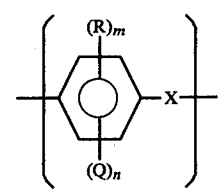

(I)

where
  each R is independently a $C_1$–$C_8$ aliphatic or a $C_5$–$C_7$ cycloaliphatic hydrocarbon radical, an aryl radical, an aralkyl radical or an alkaryl radical, each radical being free of a tertiary α-carbon atom;
  each Q is a radical of the formula

(II)

where R' is a nonpolymeric aryl radical;
X is a divalent oxygen or sulfur atom or a carbonate group;
m is an integer of 0–2; and
n is 0–1 with the proviso that n is 1 in at least 10 percent of the arylene units of the polymer.

2. The membrane of claim 1 where R' is an aryl radical of the formula

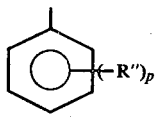

(III)

where
  each R" is independently a $C_1$–$C_6$ aliphatic radical, and
  p is an integer of 0–4.

3. The membrane of claim 2 where R' is selected from the group consisting of phenyl, tolyl, xyleneyl and phenethyl.

4. The membrane of claim 3 wherein n=1 in at least 20 percent of the arylene units of the polymer.

5. The membrane of claim 4 where x is a divalent oxygen atom.

6. The membrane of claim 5 where each R is independently a $C_1$–$C_4$ alkyl radical.

7. The membrane of claim 5 where m is 0.

8. The membrane of claim 7 where at least one of the polymers used to form the membrane consists essentially of repeating units of I.

9. The membrane of claim 8 formed from essentially only the polymer consisting essentially of repeating units of I.

10. A process of separating a gaseous mixture of $CO_2$ and $CH_4$ into enriched fractions of each, the process comprising contacting the mixture with one side of the membrane of claim 1 in such a manner that the $CO_2$ portion of the mixture is selectively passed through the membrane while the $CH_4$ portion of the mixture is selectively rejected by the membrane.

* * * * *